US010963119B1

(12) United States Patent
Alfishawi et al.

(10) Patent No.: US 10,963,119 B1
(45) Date of Patent: *Mar. 30, 2021

(54) IDENTIFYING AND RENDERING CONTENT RELEVANT TO A USER'S CURRENT MENTAL STATE AND CONTEXT

(71) Applicant: Google LLC, Mountain View, CA (US)

(72) Inventors: Thabet Alfishawi, San Francisco, CA (US); Sagar Mittal, San Francisco, CA (US); Mark Stevens, San Francisco, CA (US)

(73) Assignee: Google LLC, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/597,307

(22) Filed: Oct. 9, 2019

Related U.S. Application Data

(63) Continuation of application No. 15/651,232, filed on Jul. 17, 2017, now Pat. No. 10,481,749, which is a
(Continued)

(51) Int. Cl.
G06F 3/048 (2013.01)
A61B 5/11 (2006.01)
G06F 3/0481 (2013.01)
A61B 5/16 (2006.01)
G06F 13/00 (2006.01)

(52) U.S. Cl.
CPC ............... G06F 3/048 (2013.01); A61B 5/11 (2013.01); A61B 5/165 (2013.01); G06F 3/0481 (2013.01); G06F 13/00 (2013.01)

(58) Field of Classification Search
CPC ........ G06F 21/10; G06F 16/735; G06F 16/78; G06F 16/748; G06F 11/3414; G06F 11/3419; G06F 16/743; G06F 16/683; G06F 16/637; G08C 17/02; H04M 1/72575;
(Continued)

(56) References Cited

U.S. PATENT DOCUMENTS 9,454,289 B2 9/2016 Wheeler et al.
9,788,777 B1 10/2017 Knight
(Continued)

OTHER PUBLICATIONS

Cowei et al., Emotion recognition in human-computer interaction; IEEE, Jan 2001; 49 pages.
(Continued)

Primary Examiner — Linh K Pham
(74) Attorney, Agent, or Firm — Fish & Richardson P.C.

(57) ABSTRACT

Systems and methods are provided for identifying and rendering content relevant to a user's current mental state and context. In an aspect, a system includes a state component that determines a state of a user during a current session of the user with the media system based on navigation of the media system by the user during the current session, media items provided by the media system that are played for watching by the user during the current session, and a manner via which the user interacts with or reacts to the played media items. In an aspect, the state of the user includes a mood of the user. A selection component then selects a media item provided by the media provider based on the state of the user, and a rendering component effectuates rendering of the media item to the user during the current session.

20 Claims, 10 Drawing Sheets

Related U.S. Application Data continuation-in-part of application No. 14/556,802, filed on Dec. 1, 2014, now Pat. No. 9,712,587.

(58) Field of Classification Search
CPC .......... H04M 2250/12; H04M 1/72558; H04N 21/4307; H04N 21/47217
See application file for complete search history.

(56) References Cited

U.S. PATENT DOCUMENTS

| | | |
|---|---|---|
| 2008/0082613 A1 | 4/2008 | Szeto |
| 2010/0211966 A1 | 8/2010 | Zhang |
| 2013/0080907 A1* | 3/2013 | Skelton .............. H04N 21/4667 715/738 |
| 2013/0290843 A1 | 10/2013 | Lehtiniemi |
| 2014/0337790 A1* | 11/2014 | Kim .................... G06F 3/04842 715/781 |
| 2015/0032899 A1 | 1/2015 | Willars |
| 2015/0067708 A1 | 3/2015 | Jensen |
| 2015/0153910 A1 | 6/2015 | Wheeler et al. |
| 2015/0206523 A1* | 7/2015 | Song .................... G10H 1/0008 84/609 |
| 2015/0297109 A1 | 10/2015 | Garten |
| 2015/0318020 A1* | 11/2015 | Pribula ................ H04N 9/8205 386/227 |
| 2015/0338917 A1 | 11/2015 | Steiner |
| 2016/0065724 A1 | 3/2016 | Lee |
| 2016/0234369 A1 | 8/2016 | Jung |
| 2016/0300102 A1 | 10/2016 | Hajiyev |
| 2016/0308926 A1* | 10/2016 | Kasai ................. H04N 21/2365 |
| 2016/0335047 A1 | 11/2016 | Medaghri Alaoui |
| 2017/0046496 A1 | 2/2017 | Johnstone |

OTHER PUBLICATIONS

Yuan-Chih Yu; Design of a Mobile Telephony System for Social Interaction; IEEE; 2013; 7 pages.

* cited by examiner

United States Patent US 10,963,119 B1

IDENTIFYING AND RENDERING CONTENT RELEVANT TO A USER'S CURRENT MENTAL STATE AND CONTEXT

CROSS-REFERENCE TO RELATED APPLICATIONS

This application is a continuation of U.S. application Ser. No. 15/651,232, filed Jul. 17, 2017, which is a continuation-in-part of U.S. application Ser. No. 14/556,802, filed Dec. 1, 2014, the contents of which are hereby incorporated by reference.

TECHNICAL FIELD

This application generally relates to systems and methods for identifying and rendering content relevant to a user's current mental state and context.

BACKGROUND

Various content providers and advertisers often determine content to suggest to a user or advertisements to show to the user during a current session with the content provider based on historical analysis of the user's previous history with the content provider and/or other content providers. For example, when browsing the Internet, some advertisement systems will present the user with advertisements for content the user viewed/accessed in a previous browsing session or content similar to what they viewed or accessed in a previous session. These advertisement systems generally analyze various signals from the user's previous browsing sessions before the user begins a future browsing session to determine advertisement content to show the user in the user's future browsing session. However this advertisement content may not be relevant to the when the user begins the future browsing session for a variety of reasons.

BRIEF DESCRIPTION OF THE DRAWINGS

Numerous aspects, embodiments, objects and advantages of the present invention will be apparent upon consideration of the following detailed description, taken in conjunction with the accompanying drawings, in which like reference characters refer to like parts throughout, and in which.

DETAILED DESCRIPTION

Figure 1:
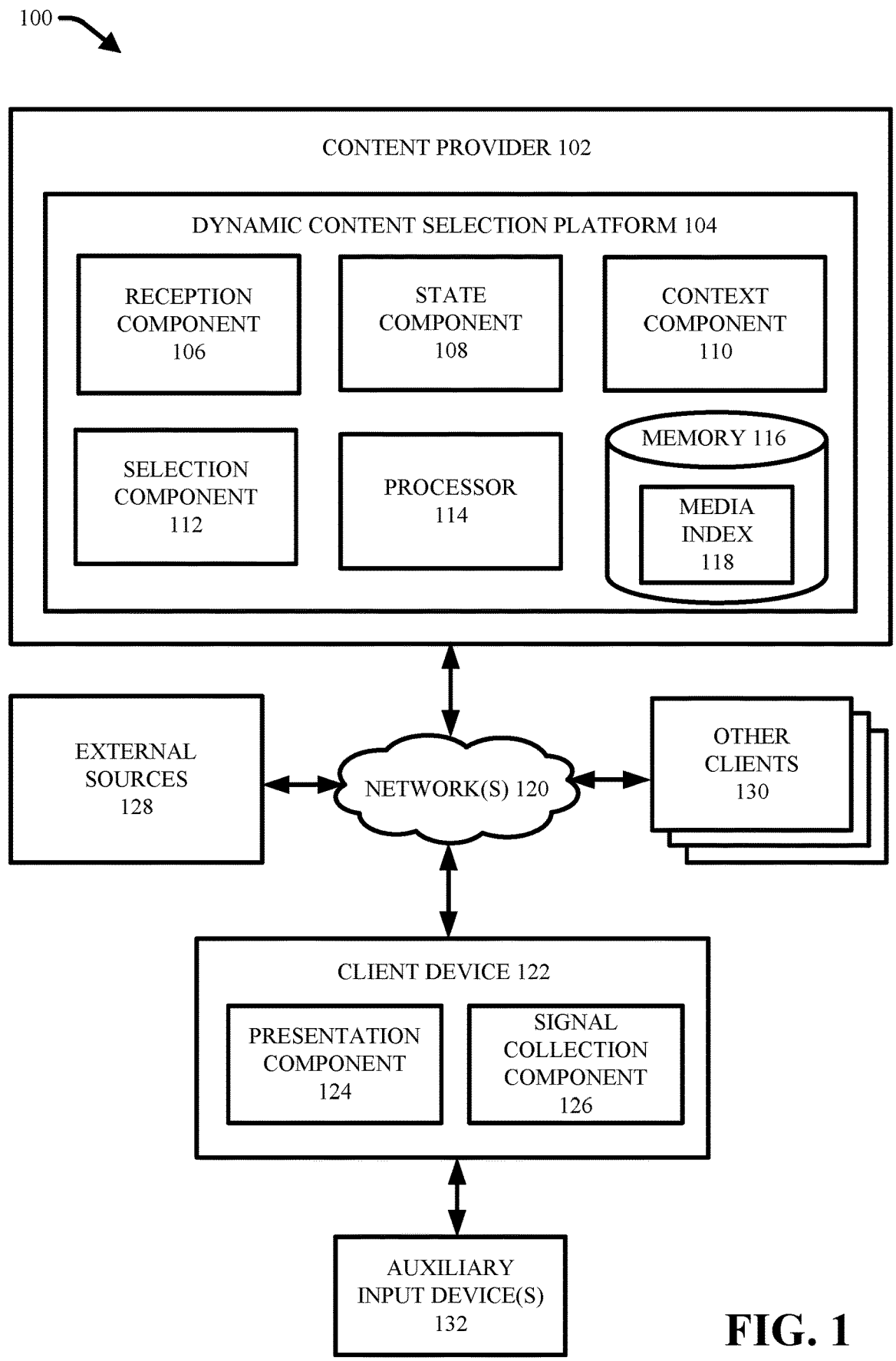
FIG. 1 illustrates an example system for identifying content relevant to a user's current mental state and context in accordance with various aspects and embodiments described herein.

The innovation is described with reference to the drawings, wherein like reference numerals are used to refer to like elements throughout. In the following description, for purposes of explanation, numerous specific details are set forth in order to provide a thorough understanding of this innovation. It may be evident, however, that the innovation can be practiced without these specific details. In other instances, well-known structures and components are shown in block diagram form in order to facilitate describing the innovation.

By way of introduction, the subject disclosure relates to dynamically determining or inferring content, provided by a content provider (e.g., via a network based platform such as a website or mobile application), that a user will be most receptive to at any given point during a current interaction session with the content provider based on the context and state of the user during the current session. Various content providers and advertisers often determine content to suggest to a user or advertisements to show to the user during a current session with the content provider based on historical analysis of the user's previous history with the content provider and/or other content providers. For example, when browsing the Internet, some advertisement systems will present the user with advertisements for content they viewed/accessed in a previous session or content similar to what they viewed or accessed in a previous session.

However, this content may not be relevant to the user during the current session for a variety of reasons. For example, during a current session, a user may not be shopping online as the user was in a prior session but researching a technical subject for a work project. Accordingly, showing content to the user during the current session that includes advertisements for products previously viewed by the user will most likely disturb and distract the user. Similarly, where the user previously accessed content related to a technical subject for a work assignment and the user is now relaxing in the evening and browsing the Internet for entertainment and leisure based content, suggesting content to the user related to the technical work subject at this time will likely annoy the user and the user will likely discard the content.

In view of the above noted drawbacks with existing techniques for identifying content to suggest or target to users, the subject disclosure employs a variety to signals received or extracted during a user's current session with a content provider to determine or infer a context of the current session and the user's mental state during the current session. These signals are then used to identify content that the user will be most receptive to at any given point during the current session. In particular, user research has shown that users are in different 'modes' according to various dynamic factors such as time of day, what device they are on, what brought them to a particular a particular content provider's website/application, where the user is located (e.g., home vs. work), how much time the user has available to interact with the website/application, what the user is doing in association with access of the website/application. In addition, depending on the type of content provided by the content provider, the user's state of mind can also influence characteristics of content that the user will be most receptive to during a current session. For example, media content (e.g., images, video, music, etc.) can evict various user emotions. When a user's current frame of mind or mood can be discerned, media content can be identified and provided to the user the reflects or effects the user's mood. Accordingly, systems and mechanisms are provided that will take into account various factors related to a user's mental state and context during a current session of the user with a content provider to determine or infer a particular content item to render to the user during the current session.

In an exemplary embodiment, the disclosed techniques are specifically tailored to determine or infer media content that a user will be most receptive to engage with during a current session with a streaming media provider that offers a wide array of different media content of various types and durations for access by the user. The specific media items that a user selects to view or listen to and the manner in which the user engages with media items selected by the user or pushed to the user can provide a strong indication of a user's mental state. For example, when a user is accessing and/or searching for short clips of funny videos, it can be inferred that the user is in a joyful, leisurely state of mind. This information coupled with information related to the context of the current session can provide even greater insight into the user's state of mind. For example, the determination that the user is in a joyful and leisurely state of mind can be held with greater confidence when it is also determined that the user is at a party sharing the videos with friends. In addition the specific content of the funny videos (e.g., the plot, the characters, the script, the setting, etc.) can give an indication of the type of humor the user enjoys during the current session.

In another example, when a user is searching for videos related to information on a specific technical subject, it can be determined that the user's frame mind is focused, diligent, serious, etc. The user's frame of mind can further be discerned depending on the time of day, location of the user, the user's profession and the specific technical subject searched. For example, the user's intentions and concerns may vary if the technical subject is related to work aspects or personal aspects. Further, the user's navigational tactics can indicate the user's intention of the current session and the user's state of mind regarding fulfilling the intention. For instance, when a user selects videos related to a specific keyword search, watches a few seconds of some of the videos in the query result, then quickly dismisses the respective videos and modifies the keyword search, it can be determined that the user is frustrated, in a hurry, and honed in on a very specific task related to understanding the technical subject.

Based on various determined or inferred features related to a user's current mental state and context during a session with the streaming media provider, media content provided by the streaming media can be identified and rendered to the user that is relevant to the current user's mental state and context. In an aspect, this media content can include advertisements (e.g., video advertisements or static advertisements). For example, a video advertisement having a specific content type and duration can be identified based on characteristics of the user's mental state and context during a current session of the user with the media provider and rendered to the user during the current session at a point during the current session when the user will be most receptive to it. In another aspect, the media content identified for provision to the user can include a trailer for another video or channel offered by the media provider. Still in yet another aspect, the media content can include other videos, playlists and channels provided by the media provider and suggested to the user in a recommendation list for viewing during the current session.

In one or more aspects, a system is provided that includes a state component configured to determine a state of a user during a current session of the user with the media system based on at least one of: navigation of the media system by the user during the current session, media items provided by the media system that are played for watching by the user during the current session, or a manner via which the user interacts with or reacts to the played media items, wherein the state of the user includes a mood of the user. The system further includes a selection component configured to select a media item provided by the media provider based on the state of the user, and a rendering component configured to effectuate rendering of the media item to the user during the current session.

In another aspect, a method is disclosed that includes using a processor to execute computer executable instructions stored in a memory to perform various acts. These acts can include: determining user state attributes associated with a user's current state of mind during a current session of the user with a streaming media provider based on at least one of: navigation of the streaming media provider by the user during the current session, media items provided by the streaming media provider that are played during the current session, or a manner via which the user interacts with or reacts to the played media items, wherein the state of the user includes a mood of the user; selecting a media item provided by the streaming media provider based on the user state attributes; and rendering the media item to the user during the current session.

Further provided is a tangible computer-readable storage medium comprising computer-readable instructions that, in response to execution, cause a computing system to perform various operations. These operations include determining mood attributes associated with a user's current mood during a session of the user with a streaming media provider and determining context attributes associated with a current context of the session based on at least one of: navigation of the streaming media provider by the user during the current session, media items provided by the streaming media provider that are played during the current session, or an environment of the user. The operations further include, selecting a media item provided by the streaming media provider based on the mood attributes and the context attributes, and rendering the media item to the user during the session.

Referring now to the drawings, with reference initially to FIG. 1, presented is diagram of an example system 100 for identifying and rendering content relevant to a user's current mental state and context in accordance with various aspects and embodiments described herein. Aspects of systems, apparatuses or processes explained in this disclosure can constitute machine-executable components embodied within machine(s), e.g., embodied in one or more computer readable ediums (or media) associated with one or more machines. Such components, when executed by the one or more machines, e.g., computer(s), computing device(s), virtual machine(s), etc. can cause the machine(s) to perform the operations described.

System 100 includes at least a content provider 102 and a client device 122 wherein the content provider is configured to provide content to a user of the client device 122 via one or more networks 120 using a network based platform (e.g., a website or mobile application). The content provider 102 can include dynamic content selection platform 104 to determine or infer characteristics of a user's current mental state and context during a session of the user with the content provider and to identify other content (e.g., an advertisement, a suggested content item, etc.) that is relevant to the user's current mental state and context. The dynamic content selection platform 104 can then facilitate rendering of the identified other content to the user by the content provider 102 during the current session. For example, when the other content is an advertisement, dynamic content selection platform 104 can direct content provider 102 to provide the advertisement to the user during the user's current session.

In various aspects, system 100 can also include external sources 128, other client devices 130 and auxiliary input devices 132. Dynamic content selection platform 104 and/or content provider 102 can include memory 116 for storing computer executable components and instructions and processor 114 to facilitate operation of the instructions (e.g., computer executable components and instructions) by the dynamic content selection platform 104. Similarly, client device 122 can include memory for storing computer executable components and instructions and a processor to facilitate operation of the instructions (not shown).

The various components and devices of system 100 can be connected either directly or via one or more networks 120. Such networks can include wired and wireless networks, including but not limited to, a cellular network, a wide area network (WAD, e.g., the Internet), a local area network (LAN), or a personal area network (PAN). For example, client device 122 can communicate with content provider 102 (and vice versa) using virtually any desired wired or wireless technology, including, for example, cellular, WAN, wireless fidelity (Wi-Fi), Wi-Max, WLAN, and etc. In an aspect, one or more components of system 100 are configured to interact via disparate networks. In addition, although dynamic content selection platform 104 is depicted as being internal to content provider 102, one or more aspects of dynamic content selection platform 104 can be provided locally at client device 122. For example, content provider 102 can include an application service provider and client device 122 can employ a thin client application to interact with and receive various content and services provided by the content provider. The thin client application provided on the client device 122 can include one or more components (e.g., reception component 106, state component 108, context component 112, etc.) of dynamic content selection platform 104.

Content provider 102 can include an entity configured to provide content and/or services to a user at a client device (e.g., client device 120) via a network (e.g., the Internet). For example, content provider 102 can include a website or application service provider configured to provide videos, pictures, articles, blogs, messages, services, etc. or other types of content items to client devices via a network. According to this example, the content provided by the website or application can be configured for downloading, streaming or merely viewing at a client device 122 via the network. In another example, content provider 102 can include a information store that provides access to data included in the information store via a network. In another example, content provider 102 can include an online merchant that provides goods and services.

As used herein, the term content item refers to any suitable data object that can be accessed or otherwise shared via a network and includes but is not limited to: documents, articles, messages, webpages, programs, applications, data object and media items. The term media item or media content can include but is not limited to: video, live video, animations, video advertisements, music, music videos, sound files, pictures, and thumbnails. In an aspect, an owner of a media item is referred to herein as a content creator to indicate that the media item was created by the content creator (i.e., the content creator holds copyright authority to the media item). In some aspects, the term media item or media content refers to a collection of media items, such as a playlist or channel including several videos or songs.

A channel can include data content available from a common source or data content having a common topic or theme. A channel can be associated with a curator who can perform management actions on the channel. Management actions can include, for example, adding media items to the channel, removing media items from the channel, defining subscription requirements for the channel, defining presentation attributes for channel content, defining access attributes for channel content, etc. In an aspect, this curator constitutes the channel owner or channel creator and the channel itself can be considered a content or media item owned or created by the channel owner.

In an aspect, channel content can include digital content uploaded to an Internet-based content platform that hosts the channel (e.g., content provider 102) by the channel curator and/or digital content selected by the channel curator from other content available on the Internet-based content platform. A channel curator can include a professional content provider (e.g., a professional content creator, a professional content distributor, a content rental service, a television (TV) service, etc.) or an amateur individual. Channel content can include professional content (e.g., movie clips, TV clips, music videos, educational videos) and/or amateur content (e.g., video blogging, short original videos, etc.). Users, other than the curator of the channel, can subscribe to one or more channels in which they are interested. Users in addition to the channel curator can access content provided by a channel.

In an exemplary embodiment, content provider 102 includes a streaming media provider configured to provide streaming media and related services to client devices over a network. For example, content provider 102 can include a media provider that has access to a voluminous quantity (and potentially an inexhaustible number) of shared media (e.g., video and/or audio) files. The media provider can further stream these media files to one or more users at respective client devices (e.g., clients 122) of the one or more users over a network. The media can be stored in memory associated with the media provider (e.g., memory 116) and/or at various servers and caches employed by media provider and accessed by client devices using a networked platform (e.g., a web site platform, a mobile application) employed by the media provider.

For example, the media provider can provide and present media content to a user via a website that can be accessed by a client device using a browser. In another example, the media provider can provide and present media to a user via a mobile/cellular application provided on a client device (e.g., where the client device is a smartphone or the like). Client device 122 can include presentation component 124 to generate a user interface (e.g., a graphical user interface or virtual interface) that displays media content provided by the media provider to a user of the client device. In an aspect, presentation component 124 can include an application (e.g., a web browser) for retrieving, presenting and traversing information resources on the World Wide Web. For example, the media provider can provide and/or present media content to a client device 122 via a website that can be accessed using a browser of the client device 122. In another example, the media provider can provide and/or present media content to a client device 122 via a mobile application platform. According to this application, presentation component 124 can employ a client application version of the media provider that that can access the cellular application platform of the media provider. In an aspect, the media content can be presented and/or played at client device 122 using a video player associated with the media provider and/or the client device 122.

Client device 122 can include any suitable computing device associated with a user and configured to interact with content provider 102 via a network. For example, client device 122 can include a desktop computer, a laptop computer, a television, an Internet enabled television, a mobile phone, a smartphone, a tablet personal computer (PC), a personal digital assistant PDA, or a wearable device. As used in this disclosure, the terms "content consumer" or "user" refer to a person, entity, system, or combination thereof that employs system 100 (or additional systems described in this disclosure) using a client device 122.

The various features of dynamic content selection platform 104 are exemplified herein wherein content provider 102 includes a streaming media provider (as described herein). Accordingly, dynamic contribution platform 104 is discussed in association with determining or inferring, in real-time or substantially real time, media content (e.g., media advertisement, video trailers, channel trailers, other videos provided by the media provider etc.) that is relevant to a user during the user's current session with the media provider. However, it should be appreciated that dynamic content selection platform 104 can be employed by a variety of content providers and systems to determine or infer content for provision to a user (e.g., advertisements, recommended content) that is relevant to the user's context and mental state at the time of rendering of the content.

In accordance with an embodiment, dynamic content selection platform 104 can include reception component 106, state component 108, context component 110 and selection component 112. Reception component 106 is configured to receive and/or extract information in association with a user's current session with content provider 102 that can be employed to determine or infer attributes of the user's current mental state and context. For example, when a user conducts a session with a streaming media provider that includes navigating and consuming media content provided by the streaming media provider, reception component 106 can receive or extract information about the user's current session that relates to the user's state of mind and context. Based on this information, state component 108 is configured to determine a state of the user and context component 110 is configured to determine a context of the user and/or the current session. Selection component 112 can then determine or infer advertisements, video trailers, channel trailers, and/or other media that the user is likely to be most receptive to during the current session based on the user's state and context.

For example, reception component 106 can receive information regarding the manner in which the user navigates the media provider's content (e.g., searching via key word search, searching within a specific media category or channel, browsing, following recommendations, etc.), the specific content accessed and viewed by the user, and the manner in which the user interacts with the content selected by the user for viewing or pushed upon the user (e.g., watching or dismissing a video, controlling the playing of the video, commenting about the video, liking or disliking the video, sharing the video, having the video visible, having the volume of the video audible, interaction with the interface via which the video is included as based on cursor movement or touch screen interaction, etc.). Reception component 106 can also receive information regarding the watch history of the user during the current session, including durations of media items selected for watching or listening to by the user and respective amounts of the media items actually watched or listened to by the user.

In an aspect, information regarding a user's navigation of a media provider, content accessed and viewed/watched, and the manner in which the user interacts with the content can be extracted in real-time as it is generated at the media provider during the user's session. In another aspect, signals regarding user interaction and engagement with the media provider during a current session can be collected at client device 122 via a signal collection component 126 and provided to reception component 106 during the course of the user's session (e.g., in real-time, in substantially real-time, or periodically). For example, signal collection component 126 can receive signals regarding cursor movement, interaction by the user with a graphical user interface via which the media provider's content is accessed, interaction and control of a media player via which video and/or audio content provided by the media provider is played, visibility of media played during a current session at the client device 122 (e.g., whether the media player is minimized/maximized, whether the media player is behind another tab or window, etc.), and volume of media played during the current session.

In another example, reception component 106 can receive information regarding a mechanism via which the current session was initiated (e.g., in response to a general request by the user to open the network based platform of the streaming media provider, or in response to selection of a link to media content, provided by the streaming media provider, at an external source 128 or received by the user in an electronic message). According to this example, reception component 106 can receive information identifying the specific media item represented by a selected link, the referral source at which the link was located (e.g., an external source 128), and information about the referral source. This information can be provided by the referring source, the client device 122 and/or identified by reception component 106 via metadata associated with the selected link and/or the referral source. For example, reception component 106 can receive information about the content of a website or webpage at which the link was located. This information can provide insight into what mood the user was in at the time of selection of the link.

Reception component 106 can also receive information related to the user's environment during a current session (e.g., including location, other people and things at the location, activities or events occurring at the location, etc.), what the user is doing in the environment in association with the current session, time of day of the current session, the type of device the user is employing to conduct the current session (e.g., mobile, stationary, tablet, phone, desktop, etc.). In an aspect, client device 122 (and other clients 130 as well) can determine its location (e.g., via a global positioning system method, triangulation, or any other suitable locating technique) and provide this location information to reception component 106 over the course of the current session. In another aspect, an external source (e.g., a cellular carrier system) can provide client location information to reception component 106. Based on received location information for client device 122 (and other clients 130), reception component 106 can look up information about the location (e.g., places and things associated with the location, events associated with the location, other clients 130/users at the location, weather at the location, traffic at the location etc.). In other aspects, information regarding a user's environment can be captured and provided to reception component 106 via an auxiliary input device 132.

In an aspect, information regarding what a user is doing in association with a current session can be received by reception component 106 from a user's schedule (e.g., provided on client device 122 or at an external source 128). In another aspect, information regarding a user's movement and motion can be captured by various motion sensors employed by the user (e.g., worn by the user) and/or provided at client device (e.g., an accelerometer, gyroscope). This motion/movement information can facilitate determining (e.g., by reception component, dynamic content selection platform 104 and/or another system), what the user is doing (e.g., walking, running, sitting, driving a car, etc.) and where the user is going. In other aspects, dynamic content selection platform 104 and/or another system can learn user patterns and behaviors over time based on where the user goes, what the user does, who the user is with, the user's schedule, etc. to determine or infer what the user is doing during a current session.

Similarly, reception component 106 can also receive information related to what the user was doing before initiation of a current session (e.g., where the user was, an activity the user was performing, etc.), an amount of time the user has for conducting the current session (e.g., the user has a one hour lunch break during after which the user must return to work and end the current session), and what the user is likely to do or scheduled to do after the current session (e.g., return to work, attend an event, etc.), based on the user's schedule and/or learned user behaviors/patterns.

Reception component 106 can also receive information about other users activity with content provider 102 during a user's current session with the content provider, wherein the other users have some connection with the user (e.g., a social connection, a shared preference, a shared demographic feature, etc.). For example, media content that is being watched, liked, shared, etc., by a user's friends at a streaming media provider while the user is conducting a current session with the streaming media provider can influence what content the user may also be interested in during the user's current session. According to this example, when a bunch of the user's friends are conducting sessions with the streaming media provider at the same time as the user and watching a particular live sports video, it can be assumed that the user would likely be interested in watching the sports video as well. Accordingly the live sports video can be recommended to the user during the user's current session.

State component 108 is configured to determine or infer state of mind attributes associated with a user's current state of mind during a session with a content provider 102 (e.g., a streaming media provider) based on information received by reception component 106. A user's state of mind can include aspects related to what the user is thinking and/or feeling during a current session. For example, state of mind attributes can correspond to aspects of a user's mood or attitude during a current session.

A user's state of mind can also reflect a user's conscious or subconscious intention for performing or conducting a session with a streaming media provider. For example, a user's mood can indicate whether the user wants to be entertained, whether the user is in an educational frame of mind, or whether the user is in a work frame of mind. In another aspect, a user's state of mind can include a level of engagement a user has with a particular content item such as a video or song (e.g., whether the user is actively attentive towards the content item or passively engaged with the content item).

In an aspect, state component 108 can determine state attributes representative of a user's current state of mind during a session with a content provider 102 based on how the user navigates about content provided by the content provider 102. For example, state component 108 can determine attributes about a user's state of mind based on how the user navigates about a media provider's website (e.g., what categories the user's selects, how the user moves from one interface to another, how the user influence what media items are presented on a particular interface, whether the user is searching or browsing, etc.). State component 108 can also determine state attributes based on media items, provided by the media provider, that are played for watching by the user during the current session (e.g., either in response to selection by the user or automatically played/pushed to the user), and a manner via which the user interacts with or reacts to the played media items.

For instance, if a user is accessing funny videos about puppies, the user is likely in a happy mood. In addition, if the user is liking, sharing, and providing positive comments about the funny videos, it can be discerned that the content brings the user joy and entertainment. Accordingly, state attributes for the user could include 'happy,' 'joyful,' entertainment mode,' 'humorous content,' and 'light hearted.' In another example, if a user is selecting or searching for music playlists with classical music, state component 108 can determine the user is in a relaxed mood. In another aspect, based on the type of media content a user selects for watching/listening to, state component 108 can determine whether the user is looking to be entertained and how or whether the user is looking for informational/instructional content. For instance, when a user is selecting videos that are short movies of a thriller genre, state component 108 can determine the user is looking to be entertained with media content that has a thriller theme. According state attributes for the user could include 'entertainment mode,' 'movie,' and 'thriller.' In another example, if a user is selecting exercise videos, state component 108 can determine that the user is in a mindset of working out.

In an aspect, respective media items provided by a media provider at which a user conducts a current session can be associated with one or more different mood or state of mind attribute values. In an aspect, these mood or state of mind attributes can be associated with the respective media items as metadata associated with the respective media items. In another aspect, these mood or state attributes can be associated with the respective media items on a database correlating the respective media items to mood/state of mind attributes. For example, a funny video about puppies can be associated with mood values of corresponding to happy, joyful, sappy, sensitive, and humorous. In another example, workout videos can be associated with moods reflective of exercise, motivation, health and energy. In another example, classical music based content can be associated with relaxation mood values. In yet another example, attributes of media items provided by the media provider (e.g. videos, channels, playlists, songs, etc.) related to a type of the media item (e.g., movie, sitcom, advertisement, music video), and a genre of the media item (e.g., comedy, drama, romance, thriller, reality, instructional, informational, etc.) can be associated with respective mood values. According to this aspect, state component 108 can analyze the various state or mood values associated with media items viewed (e.g., watched and/or listened to) by a user over the course of a current session to determine or infer one or more cumulative state attributes of the user's mood.

In addition, information regarding a level of user interaction and engagement with the respective media items can further facilitate determining a user's mood. For example, where a user engages with and interacts more with media items having mood values of a, b, and c and less with media items having mood values x, y and z, state component 108 can place a greater weight on mood values a, b and c when determining the user's mood attributes.

In another aspect, state component 108 can determine or infer a user's mood based on the manner in which a user navigates content provided by a media provider during the user's session with the media provider. For example, based on the user's navigational mechanisms, state component 108 can whether the user is in a state of haste or whether the user is not in a state of haste. According to this example, state component 108 can determine or infer that a user is in a state of haste or not based on how quickly and frequently a user selects new media items for viewing and the durations of the media items selected for viewing being relatively short or long (e.g., with respect to a threshold duration) as well as the amounts of the durations watched/listened to by the user (e.g., watching more than X % of a video can indicate the user is not in a state of haste while watching less than X % of a video can indicate the user is in a state of haste).

In another example, based on the user's navigational mechanisms, state component 108 can determining whether the user is in a leisurely mindset or has is focused on a specific agenda or task. According to this example, when a user's navigation mechanisms indicate the user is browsing the various media content provided by a media provider (e.g., via selecting recommended media items or items associated with different media item categories), state component 108 can consider the user in a leisurely mindset. On the other hand, when a user is performing a specific keywords search and looking for videos of a particular subject matter or title, the user can be considered to be in focused and structured mindset. Accordingly, based on a user's navigational mechanisms, state component 108 can determine or infer state attributes to associated with a user during a current session that include 'state of haste or hurry,' 'browsing mindset,' 'focused searching mindset,' 'structure searching mindset,' and similar attributes.

In another aspect, state component 108 can determine or infer attributes associated with a user's state of mind based on the manner via which a user interacts with or reacts to the media items played during the user's current session. For example, if a user stops playing a certain media item or disengages from the media item as it plays, state component 108 can determine that mood values associated with the media item do not reflect the user's current mood. Similarly, where a user engages with a particular media item during a current session, shares the media item, comments on the item etc., state component 108 can determine or infer that mood values associated with the media item are more reflective of the user's current mood. Thus in an aspect, state component 108 can weight mood values associated with media items accessed/watched/listened to by a user based on the manner and level of engagement the user has with the respective media items.

In another aspect, state component 108 can determine or infer attributes corresponding to a user's current state of mind based on comments provided by the user about the media item ("I love this song," "this was so scary," "this video made be bawl," etc).

In another aspect, a user's state of mind can include a level of engagement of a user during a current session with a media provider and/or particular content played during the session. For instance, state component 108 can determine or infer state attributes that indicate whether the user is actively engaged, passively engaged or disengaged. In an aspect, state component 108 can discern a user's level of engagement during a current session based on explicit engagement signals (e.g., like/dislike, comment, subscribe, seek, etc.) and implicit engagement signals (e.g., continued playback, mouse/keyboard movement, device movement, touchscreen activity, etc.) received by reception component 106. In an aspect, state component 108 can determine a user's level of engagement during a current session based on visibility of the played media items via an interface presented to the user during the current session and volume of the played media items. For example, when a user has video content playing with the volume turned off or low, state component 108 can determine that the user is passively engaged in a 'watching no volume mode.' In another example, when a user has a video content playing with the volume turned up yet the video player minimized or provided behind another open window or tab, state component 108 can determine that the user is passively engaged in a 'listening only mode.' However where both the video player is not visible and the volume is turned off or down, state component 108 can determine that the user is disengaged.

Further, state component 108 can employ information regarding a user's movement/motion to determine or infer a user's state of mind. For example, if a user is moving or headed somewhere, state component 108 can determine that the user is in a state of 'haste' or 'on the go.' Similarly, if the user is stationary, state component 108 can determine that the user is relaxed and has time on his hands.

Context component 110 is configured to determine context characteristics related to the context of a current session between a user and content provider 102. Context refers to the circumstances that form the setting for an event, statement, or idea, and in terms of which it can be fully understood and assessed. With respect to a current session between a content provider, (such as a streaming media provider) and a user, context can include the circumstances that form the setting of the current session. In an exemplary embodiment, context component 110 is configured to determine context characteristics associated with a current session between a user and a media provider based on information received by reception component 106. In an aspect, these context characteristics can include but are not limited to: where the user is located or going during the current session (e.g., as determined by context component 110 based on received or determined location information for client device 122 during the current session and/or received user movement/motion information), when (e.g., time of day) the current session is occurring, and who the user is with (e.g., alone, with a group other users, with a friend etc.) during the current session (e.g., as determined by context component 110 based on received location information for other clients 130 when authorized by the other clients). In addition, based on a user's location, content component 110 can further employ various external sources to look up current context characteristics about the location (e.g., persons, places, things, events, weather, traffic, etc. associated with the location). For example, context component 110 can determine that a user is located at a restaurant at a time when the restaurant that is throwing special event for alumni of a local college.

In another aspect, context component 110 can determine or infer content characteristics that relate to what a user is doing aside from or in association with a current session with a content provider (e.g., walking, exercising, riding a train/bus, working, conducting a work meeting, attending a class, cleaning the house, attending a party with friends, etc.). Context component can also determine characteristics regarding what the user was doing before and/or will do after the current session. For example, context component 110 can determine or infer an activity performed by the user preceding initiation of the current session, a duration of time the user has available for the current session, or an activity for performance by the user at a known point in time after initiation of the current session. Context component 110 can determine these content characteristics related to what a user is doing, was doing and will do in the near future based on analysis of a various received signals related to where the user is located, time of day, what device the user is on, and movement data for the user in view of the user's schedule and/or learned behavior for the user. For example, based on information indicating the user is located at her home around 6 am on a weekday morning, information indicating the user is moving about the house, information indicating the user is conducting a current media session on her Internet enabled television, and the user's work schedule, context component 110 can determine that the user is getting ready to go to work and will be leaving the house at about 7 am.

Context component 110 can also determine content characteristics related to a user's purpose for a current session. For example, context component 110 can determine whether a current session with a media provider is for an entertainment purpose, an educational purpose, or a work related purpose. In an aspect, context component 110 can determine or infer a purpose of a current session with a media provider based on the media items provided by the media system that are played for watching by the user during the current session, and the manner via which the user interacts with or reacts to the played media items. For example, context component 110 can determine whether a user is performing the current session to get information about a specific subject, to find a playlist for a party, to watch videos about a particular subject, to get the recent local news, to find a movie to watch, to browse for something entertaining to watch, to get instruction for performing a task, to find a yoga instruction video, etc.

In an aspect, context component 110 can determine a purpose for a current session with a media provider based on how the current session was initiated. For example, the purpose of a session could initially include a user's desire to view a media item represented by a selected link at another source. According to this example, context component can determine 110 whether the user was directed to the media system from a referral source, a media item provided by the media provider represented by a link selected by the user at the referral source, and/or information about the referral source.

Further, context component 110 can determine or infer information related to sessions of other users, related to the user (e.g., friends of the user, users sharing similar preferences or demographics of the user, etc.), with the content provider that are being conducted during the current session of the user. For example, context information regarding content the user's friends are accessing and sharing while the user is also accessing the content provider can influence what the user may find interesting during the user's current session, such as what videos and channels the user's friends are watching during the user's current session with a media provider.

In various aspects, state component 108 can determine or infer various attributes about a user's state of mind based on characteristics of a user's context as determined by context component 110. In particular, a user's context can greatly influence the user's state of mind. For example, a user's mood can vary depending on the time of day, the user's environment (e.g., where the user is located and current aspects associated with the location at the time of day and day of week, including other persons, things and events or activities), what the user is doing in association with the current session (e.g., driving, relaxing, at a party, etc.), what the user just did before the session and/or has to do after the session, what device the user is employing, or how the user initiated the session (e.g., in response to selection of a link to a specific video, to conduct a search, or to browse). In various aspects, state component 110 can analyze characteristics about a user's context to facilitate determining or inferring a user's current state of mind (e.g., mood, attitude, emotional state, energy level, etc.). For example, state component 108 can employ various rule based classification schemes and/or machine learning techniques that relate different context attributes associated with a user's current context particular to state of mind attributes (e.g., mood values).

Selection component 112 is configured to select a content item for provision to a user during the user's current session with a content provider 102 based on the various state attributes and context characteristics determined or inferred by state component 108 and context component 110, respectively, during the user's current session. In an exemplary embodiment, where content provider 102 is a streaming media provider, selection component 112 is configured to select a media item based on the user's state attributes and context characteristic. For example, the media item can include a media advertisement or video trailer for another media item or channel provided by the media provider. According to this example, the media advertisement or video trailer can be provided to the user (e.g., as an in-stream advertisement/trailer, as a banner advertisement, as an in-video advertisement, etc.) to the user in association with other media content accessed by the user during the current session. In another example, the media item can include another media item provided by the media provider. According to this example, the media item can be provided to the user in a recommendation section or list of media items recommended to the user during the user's current session.

In an aspect, selection component 112 can employ a media index 118 that associates a plurality of media items and media advertisements, provided by the media provider, with state attributes and context attributes. The state and context attributes associated with a particular media item can be selected based on a particular user a state of mind and user context under which the media item is considered to be well received. For example, a video advertisement for a fast food breakfast restaurant could be associated with state attributes such as 'hungry,' 'state of haste,' 'tired,' or 'on the go.' Context attributes associated with the advertisement could include 'morning,' 'driving,' and 'location N' (wherein location N can vary and include different locations where the fast food breakfast restaurant is located). In another example, media items in media index 118 can be associated with various mood attributes indicative of modes the media items evoke or compliment, such as mood attributes indicating whether the media item is suited for users in an entertainment related or a work related mode. In another example, media items that are relatively short in length (based on a threshold length) can be associated with attributes that indicate they are suited for users who are in a state of haste/hurry or in distracted/passive state while media items that are longer in duration can be associated with attributes that indicate they are suited for users who are in leisurely, calm, time on their hands, attentive, etc., kind of state. In yet another example, a media advertisement can be associated with attributes that indicate whether it has audible branding or not (wherein a media advertisement without audible branding will be ineffective for a user who is passively engaged with a media content session based on failure to have a media player or interface visible to the user). Similarly, a media advertisement can be associated with an attribute indicating it has no or low visible branding (wherein the media advertisement will be ineffective when the user is passively engaged do to no or low volume).

According to this aspect, selection component 112 can match or relate user state attributes and user context characteristics with state attributes and context characteristics associated with different media items provided in media index 118 to identify one or more media items that match or relate the user's current state of mind and context. For example, when a user is relaxing in the evening at home and selecting and watching relatively short videos with funny and light hearted content, selection component 112 can select a media item for provision to the user that is also relatively short and has an entertaining, funny and light hearted nature.

In an aspect, a determination that a media item matches a user's current state and context can be based on a correspondence threshold (e.g., a percentage match threshold) between the user's current state and context attributes and the state and context attributes associated with the media item. The degree of contribution of certain state attributes and context characteristics to a match determination can also vary. For example, a location based context characteristic can provide a greater influence on a match determination over a context characteristic related to why a user's current session was initiated. In another aspect, selection component 112 can be configured to select media items that do not necessarily share the same state/context attributes as a user, but which are associated with state/context attributes that compliment those of the user. For example, where a user is in a sad mood in association with a cold winter weather, rather that identifying a media advertisement that is reflective of sad and cold winter weather attributes, selection component can identify a media advertisement that is associated with attributes designed to lift the user's spirits. For example, a suitable advertisement could include one for a warm weather vacation.

In other aspects, selection component 112 can employ various rule based classification schemes or machine based learning techniques to facilitate selecting a media item that a user will likely be receptive to and engage with during the user's current session with a media provider based on the user's current state of mind and context. In furtherance to the above example, selection component 112 can infer that although a user's state and context characteristics indicate the user is a relatively good match for the fast food breakfast restaurant advertisement, based on a single context characteristic that indicates the user has X amount of time before she has to be at work, the user will not be able to stop at the fast food breakfast restaurant on the way to work. Accordingly, selection component 112 can determine that provision of the fast food breakfast restaurant advertisement to the user during the user's current session would not cause the user to act on the advertisement, and thus select a different media advertisement for provision to the user.

Figure 2:
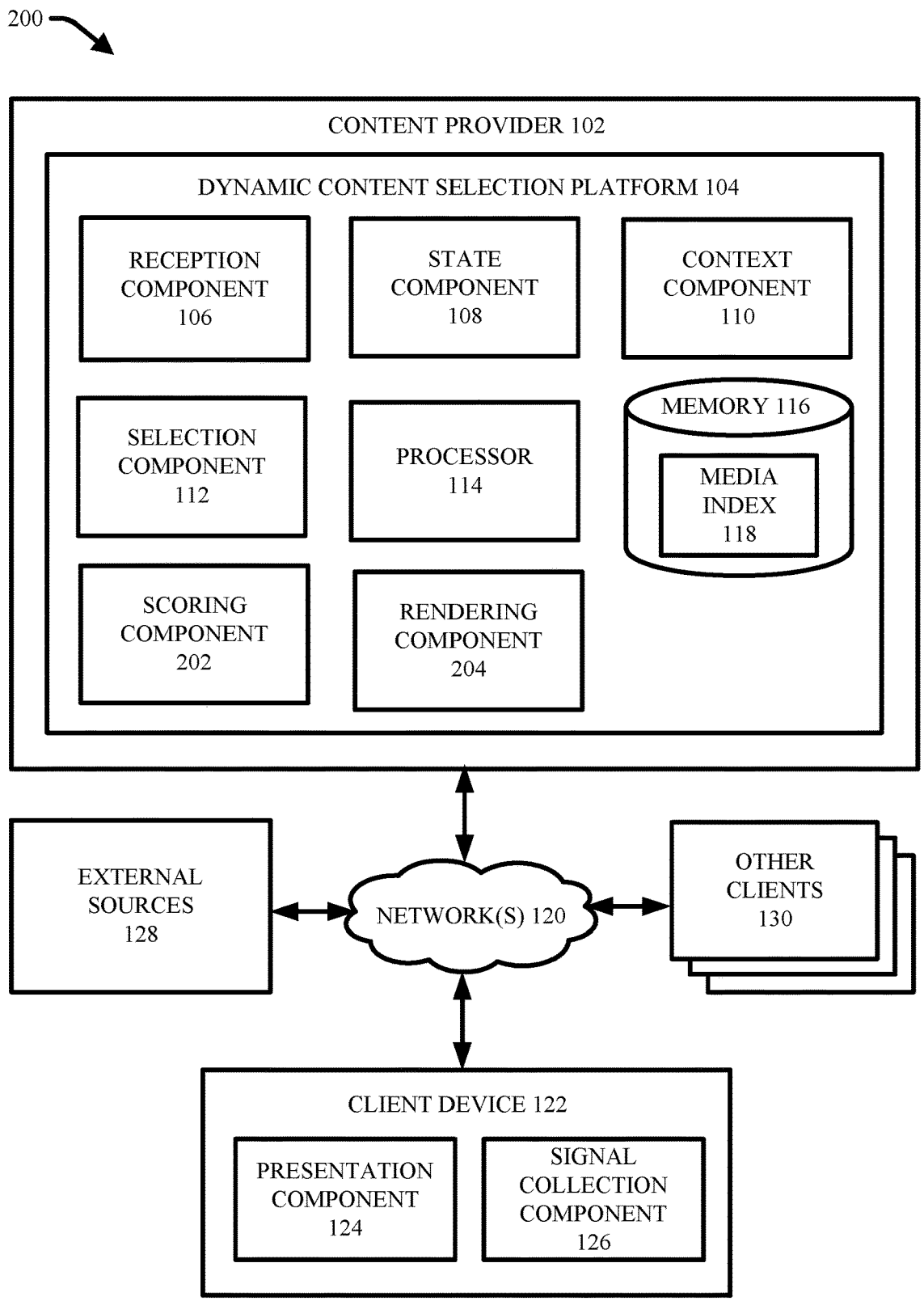
FIG. 2 presents an example system for identifying and rendering content relevant to a user's current mental state and context in accordance with various aspects and embodiments described herein.

Referring now to FIG. 2 presented is another example system 200 for identifying and rendering content relevant to a user's current mental state and context in accordance with various aspects and embodiments described herein. System 200 includes same or similar features and functionalities as system 100 with the additions of scoring component 202 and rendering component 204 to dynamic content selection platform 104. Repetitive description of like elements employed in respective embodiments of systems described herein is omitted for sake of brevity.

Scoring component 202 is configured to score and rank content items (e.g., media items) provided by content provider 102 (e.g., a streaming media provider based on relevance or suitability to a user in association with a current session between the user and the content provider 102, wherein the determination of relevance or suitability is based at least in part on the user's current state of mind and context. For example, scoring component 202 can score media advertisements provided by a media provider based on relevance and suitability of the media advertisements for a user during the user's current session with the media provider based on the user's current state of mind and context. In an aspect, scoring component 202 can analyze a plurality of media advertisements based on correspondence and fixed relationships between the user's current user state and context attributes and state and context attributes respectively associated with the media advertisements to determine a score for the respective media advertisements representative of relevance and suitability of the respective media advertisements to the user. According to this example, relevance and suitability can reflect a probability that the user will view the advertisement and/or the advertisement will have an impression upon the user. Selection component 112 can then select the media advertisement having the highest score (and/or a subset of the media advertisement having the highest scores) for provision to the user during the user's current media session.

For example, scoring component 202 can evaluate each pairing between a user and a potential media advertisement by putting the advertisement state and context attributes and the user's current state and context attributes into a 1xN boolean feature vector:

$$F=\langle f_1, f_2, \ldots, f_N \rangle$$

wherein each attribute or feature (e.g., user is active, user is A, user is B . . . , advertisement is X, advertisement is Y, . . . , user has mood X, advertisement has mood Y, etc.) is assigned a fixed position. Then scoring component 202 can score a particular advertisement/user pairing by taking the dot product with a weight vector W $$F \cdot W = S$$

where S is the score. The weight vector W can be designed to account for a probability that the media advertisement will be viewed past a billable point and/or a probability that the media advertisement will have a lasting impression upon the user. In an aspect, W can be generated using historical data using a machine learning algorithm.

In addition, as attributes for a user's current state of mind and context change over the course of a user's session with a media provider, scoring component 202 can re-score the respective media advertisements based on the new user attribute values. Accordingly, over the course of the user's session, selection component 112 can dynamically select the most relevant and suitable media advertisement for provision to the user at a current point in the user's session based on the user's current mental state and context at that point.

In another example, scoring component 202 can score and rank trailers for channels provided by a media provider or trailers for other videos provided by the media provider based on relevance and suitability for a user during the user's current session with the media provider in view of the user's current state of mind and context. According to this example, relevance and suitability can reflect a probability that the user will view the trailer and choose to select the channel or video represented by the trailer for watching, subscribing to, or otherwise showing an affinity for. In an aspect, selection component 112 can then select the trailer having the highest score (and/or a subset of the media advertisement having the highest scores) for provision to the user during the user's current media session. It is to be appreciated that respective scores associated with trailers can change over the course of a user's media session based on changes to the user's mood or context. Accordingly, at any given time in a user's media session, selection component 112 can select the trailer having the highest score at that time.

In yet another example, scoring component 202 can score other media items (e.g., videos, channels or playlists) provided by a media provider based on relevance and suitability for a user during the user's current session with the media provider based on the user's current state of mind and context. According to this example, relevance and suitability can reflect a probability that the user will view/play the media item or subscribe to the media item. Selection component 112 can then select a subset of media items having the highest scores for provision to the user in a recommendation section/list during the user's current media session.

Rendering component 204 is configured to effectuate the rendering of a content item (e.g., a media item) identified be selection component 112 to the user during the user's current session. For example, when the session includes a session with a streaming media provider, rendering component 204 can direct the streaming media provider to stream a selected video advertisement or trailer (e.g., an in-stream video advertisement) to the user in association with another media item accessed by the user. In another example, rendering component 204 can direct the streaming media provider to include a subset of media items identified by selection component 112 in a recommendation menu or list included in a portion of a user interface employed by the streaming media provider.

Figure 3:
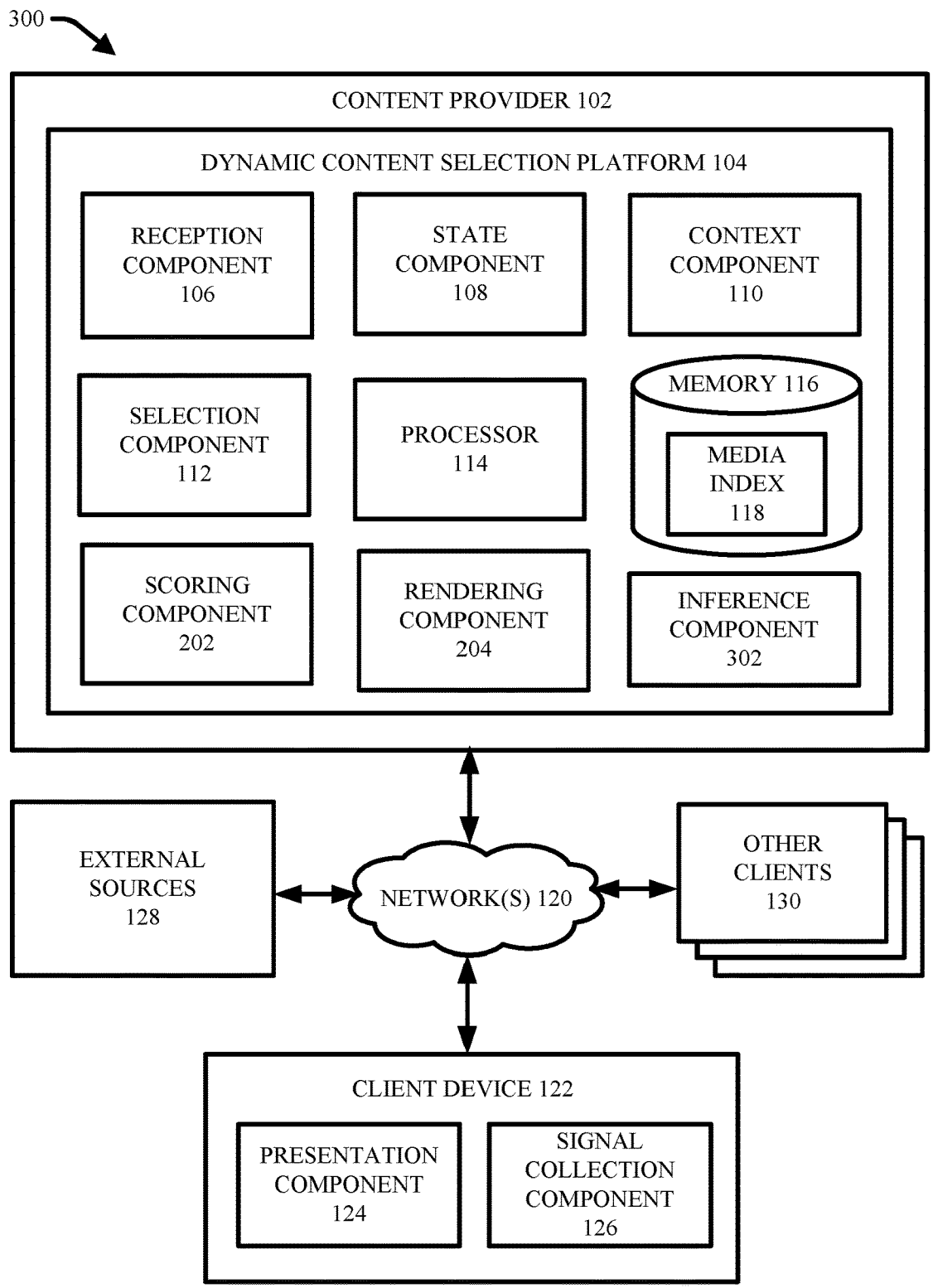
FIG. 3 presents another example system for identifying and rendering content relevant to a user's current mental state and context in accordance with various aspects and embodiments described herein.

FIG. 3 presents another example system 300 for identifying and rendering content relevant to a user's current mental state and context in accordance with various aspects and embodiments described herein. System 300 includes same or similar features and functionalities as system 200 with the addition of inference component 302 to dynamic content selection platform 104. Repetitive description of like elements employed in respective embodiments of systems described herein is omitted for sake of brevity.

Inference component 302 is configured to provide for or aid in various inferences or determinations associated with aspects of dynamic content selection platform 104. For example, inference component 302 can aid state component 108 and context component 110 with inferring attributes about a user's current state of mind and context based on the various information received by reception component 106 discussed herein. In addition, inference component 302 can aid selection component 112 with identifying a content item (e.g., a media item) that is likely to be well received by a user during the user's current session based on the user's current state of mind and context. Similarly, inference component 302 can facilitate scoring component 202 with inferring scores of suitability and relevance for content items based on a user's current state of mind and context and state and context attributes respectively associated with the content items.

In order to provide for or aid in the numerous inferences described herein, inference component 302 can examine the entirety or a subset of the data to which it is granted access and can provide for reasoning about or infer states of the system, environment, etc. from a set of observations as captured via events and/or data. An inference can be employed to identify a specific context or action, or can generate a probability distribution over states, for example. The inference can be probabilistic—that is, the computation of a probability distribution over states of interest based on a consideration of data and events. An inference can also refer to techniques employed for composing higher-level events from a set of events and/or data.

Such an inference can result in the construction of new events or actions from a set of observed events and/or stored event data, whether or not the events are correlated in close temporal proximity, and whether the events and data come from one or several event and data sources. Various classification (explicitly and/or implicitly trained) schemes and/or systems (e.g., support vector machines, neural networks, expert systems, Bayesian belief networks, fuzzy logic, data fusion engines, etc.) can be employed in connection with performing automatic and/or inferred action in connection with the claimed subject matter.

A classifier can map an input attribute vector, x=(x1, x2, x3, x4, xn), to a confidence that the input belongs to a class, such as by f(x)=confidence(class). Such classification can employ a probabilistic and/or statistical-based analysis (e.g., factoring into the analysis utilities and costs) to prognose or infer an action that a user desires to be automatically performed. A support vector machine (SVM) is an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

Figure 4:
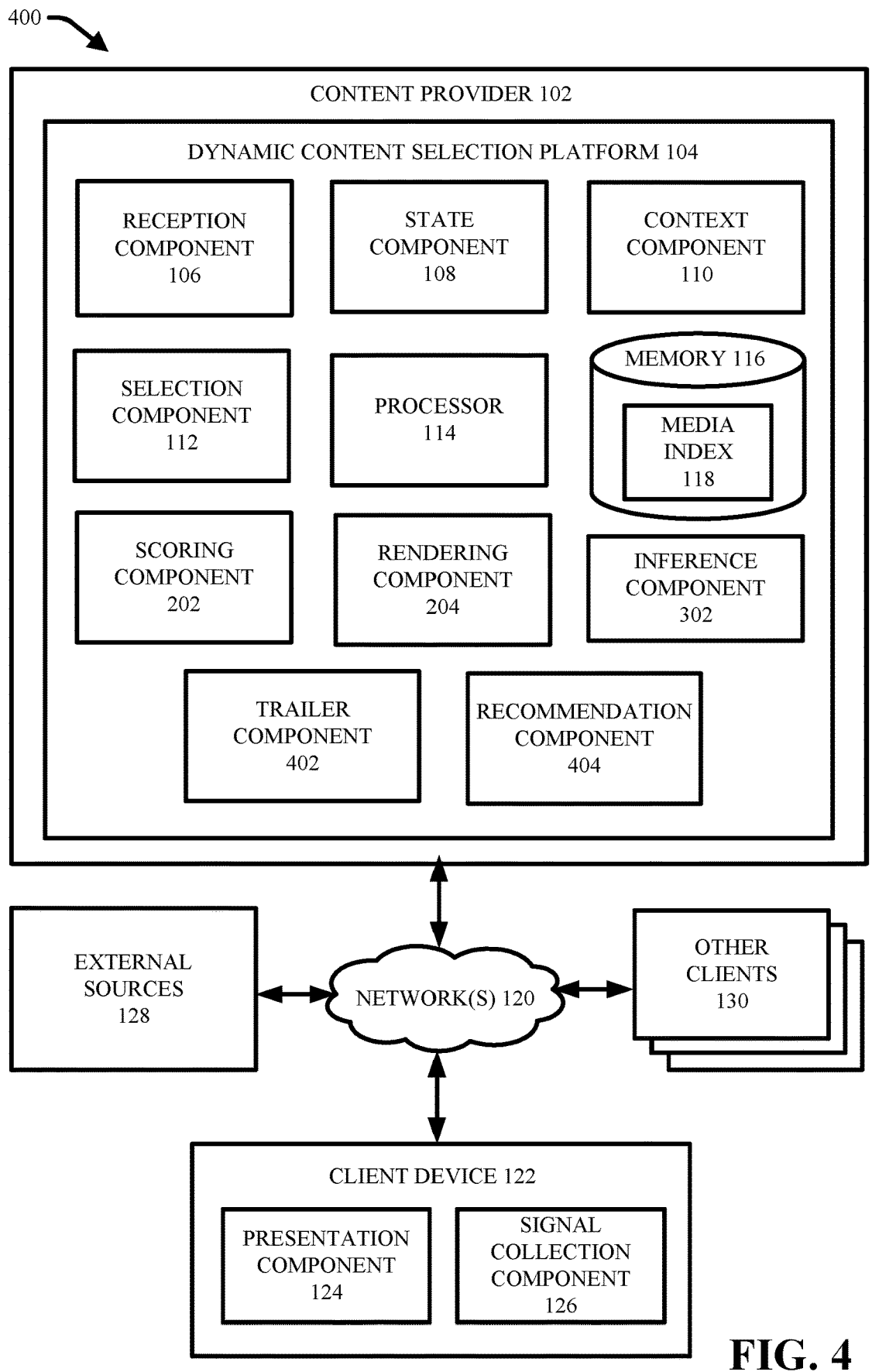
FIG. 4 presents another example system for identifying and rendering content relevant to a user's current mental state and context in accordance with various aspects and embodiments described herein.

FIG. 4 presents another example system 400 for identifying and rendering content relevant to a user's current mental state and context in accordance with various aspects and embodiments described herein. System 400 includes same or similar features and functionalities as system 300 with the additions of trailer component 402 and recommendation component 404 to dynamic content selection platform 104. Repetitive description of like elements employed in respective embodiments of systems described herein is omitted for sake of brevity.

As previously discussed, selection component 112 is configured to select a content item for provision to a user during the user's current session with a content provider 102 based on the user's current state of mind and context. The type of the content item selected can vary depending on the content provider 102. In an aspect, where content provider 102 is a streaming media provider, the content item can include a trailer for another media item provided by the streaming media provider. In video and film terminology a trailer is a series of short edited clips of selected scenes of a video that are put together into one montage. Trailers are often used as a way to advertise a video or film. Trailer for channels provided by the streaming media provider can include video content associated with the channel configured to provide a video advertisement for the channel.

Trailer component 402 is specifically configured to identify video and/or channel trailers for videos and channels provided by a media provider based on a user's current state of mind and/or context during a current session with the media provider. In an aspect, a trailer identified by trailer component 402 can be streamed to a user during the user's current session as an in-stream video in association with another video selected for watching by the user. In another aspect, a trailer identified by trailer component 402 can be streamed to a user during the user's current session when the user is not playing another video (e.g., while the user is searching or browsing for media items provided by the media provider.

Recommendation component 404 is configured to generate a list of recommended media items, provided by a streaming media provider, for suggesting or recommending to a user during a user's current session with a streaming media provider based on the user's current state of mind and/or context. For example, recommendation component 404 can identify videos, channels, and/or playlists that include media content that is reflective of or complementary to a user's current mood and context.

Figure 5:
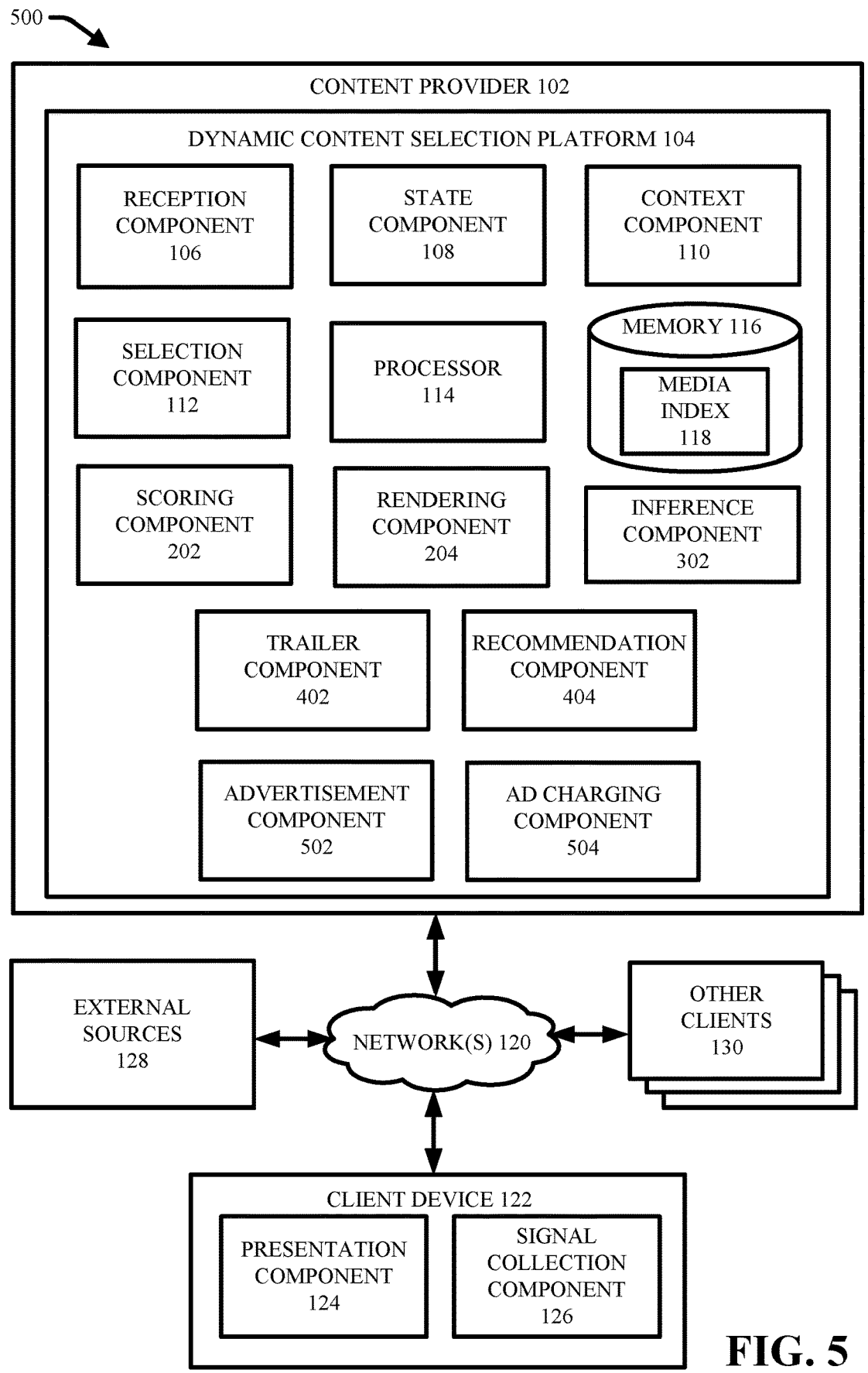
FIG. 5 presents another example system for identifying and rendering content relevant to a user's current mental state and context in accordance with various aspects and embodiments described herein.

FIG. 5 presents another example system 500 for identifying and rendering content relevant to a user's current mental state and context in accordance with various aspects and embodiments described herein. System 500 includes same or similar features and functionalities as system 400 with the additions of advertisement component 502 and advertisement charging component 504 to dynamic content selection platform 104. Repetitive description of like elements employed in respective embodiments of systems described herein is omitted for sake of brevity.

Advertisement component 502 is configured to facilitate targeted advertising based on a user's current state of mind and context during a session with a content provider 102. For example, advertisement component 502 can identify video advertisements, banner advertisements, image advertisements, audio advertisements, etc. that are relevant to a user and likely to provide an impression upon the user based on the user's current state of mind and context as determined or inferred by state component 108 and context component 110, respectively. As a result, advertisement component 502 can target users with tailored advertisements at the right time, increasing user happiness and advertiser return on investment.

Advertisement charging component 504 can facilitate dynamically charging an advertiser for provision of an advertisement based on a degree to which the advertisement capitalizes on a user's current state of mind and context. For example, in an aspect, scoring component is configured to dynamically score advertisements based on relevance and suitability of the advertisements for a user given various attributes associated with the user's state of mind and context, wherein relevance and suitability can reflect a probability that the user will view the advertisement and/or the advertisement will have an impression upon the user. Advertisement charging component 504 can factor in an advertisements score in association with charging provision of the advertisement.

Figure 6:
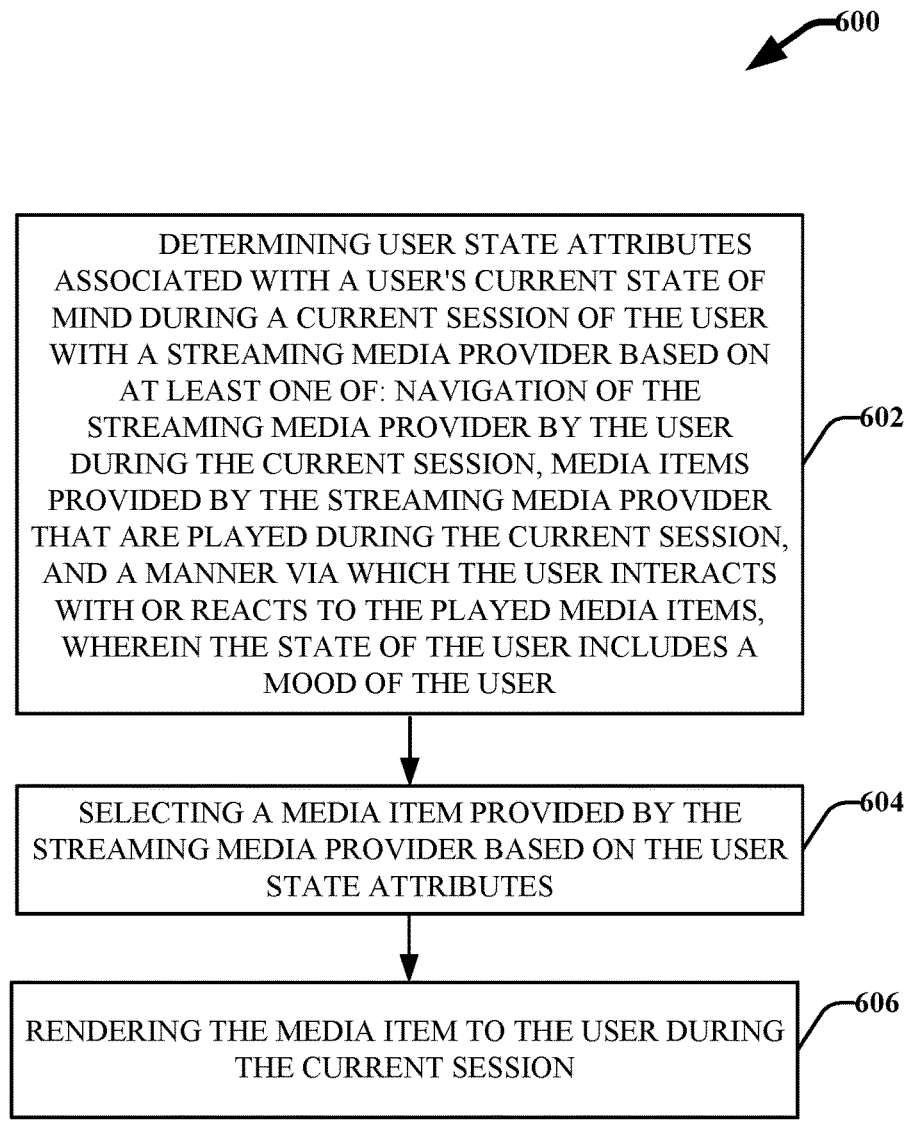
FIG. 6 illustrates an example flow diagram of an example method for identifying and rendering content relevant to a user's current mental state and context in accordance with various aspects and embodiments described herein.
Figure 7:
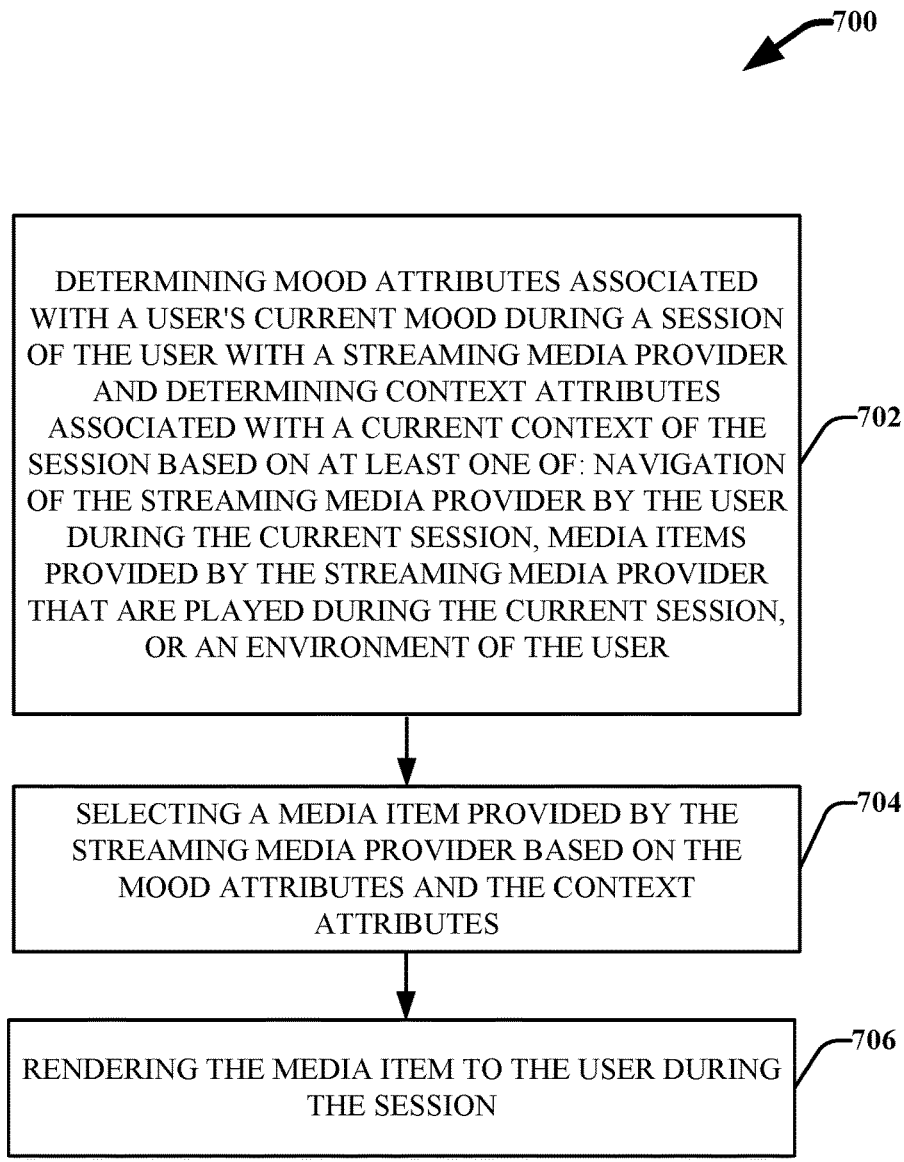
FIG. 7 illustrates another example flow diagram of an example method for identifying and rendering content relevant to a user's current mental state and context in accordance with various aspects and embodiments described herein.
Figure 8:
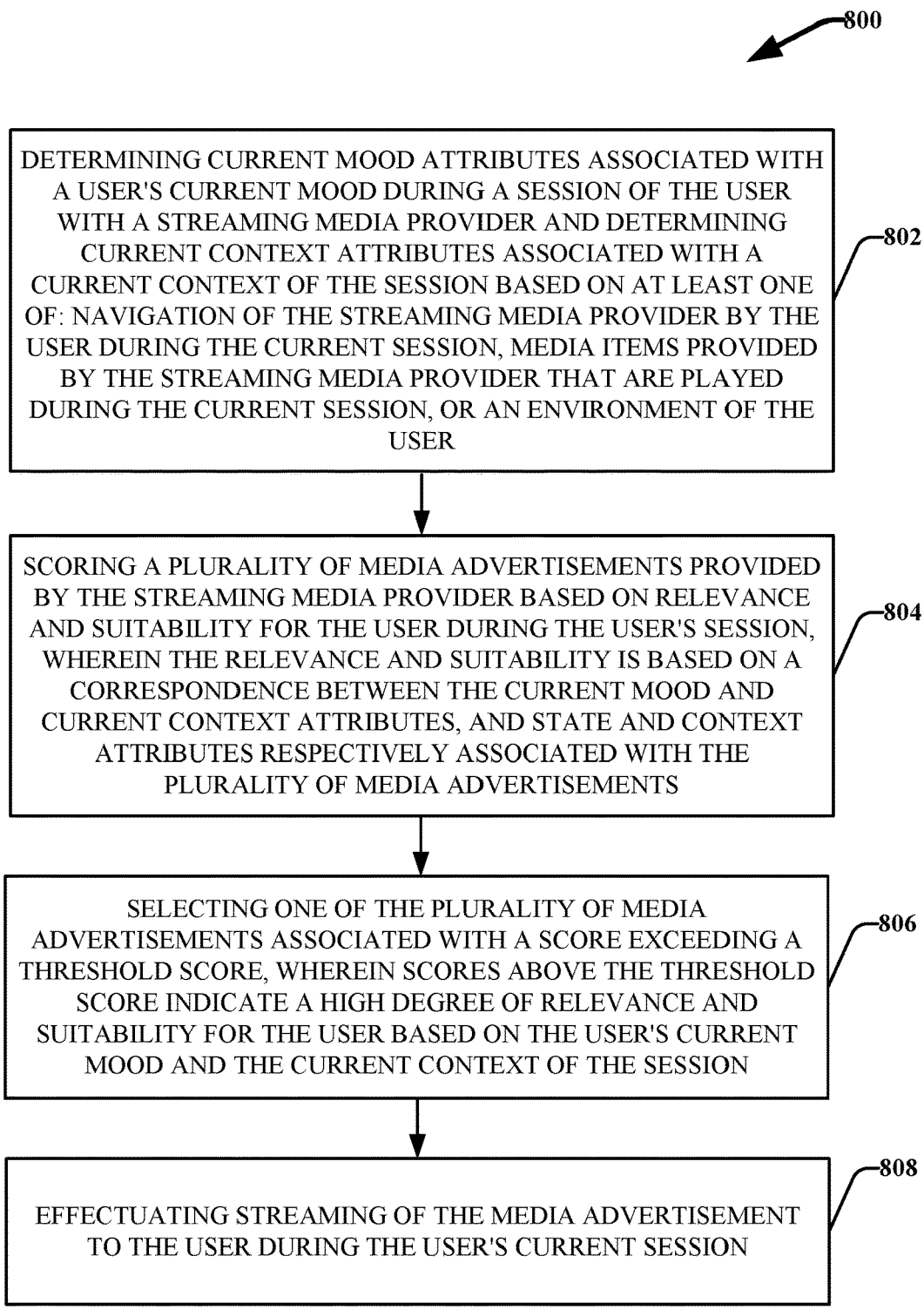
FIG. 8 illustrates another example flow diagram of an example method for identifying and rendering content relevant to a user's current mental state and context in accordance with various aspects and embodiments described herein.
Figure 9:
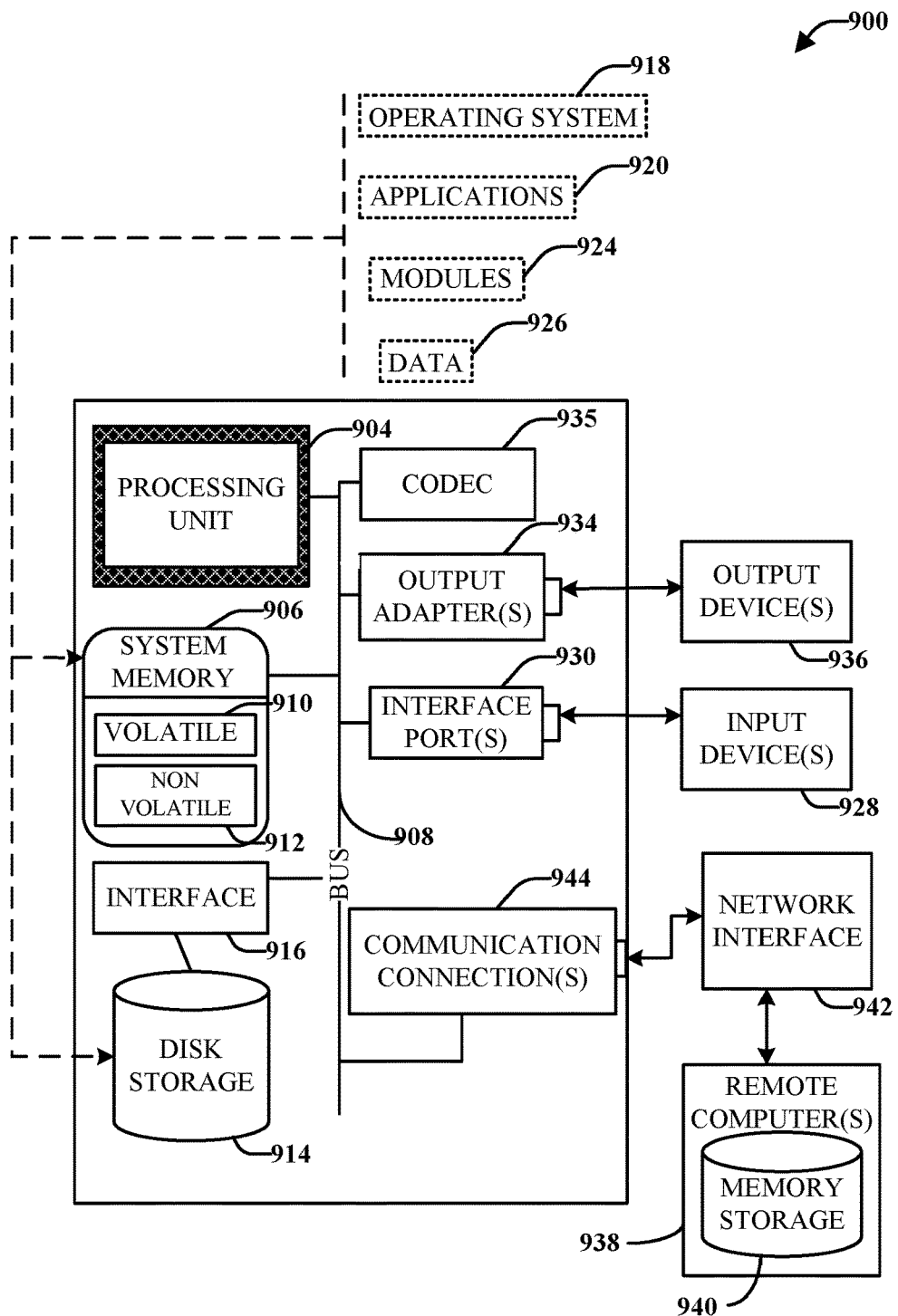
FIG. 9 is a schematic block diagram illustrating a suitable operating environment in accordance with various aspects and embodiments.

In view of the example systems and/or devices described herein, example methods that can be implemented in accordance with the disclosed subject matter can be further appreciated with reference to flowcharts in FIGS. 6-8. For purposes of simplicity of explanation, example methods disclosed herein are presented and described as a series of acts; however, it is to be understood and appreciated that the disclosed subject matter is not limited by the order of acts, as some acts may occur in different orders and/or concurrently with other acts from that shown and described herein. For example, a method disclosed herein could alternatively be represented as a series of interrelated states or events, such as in a state diagram. Moreover, interaction diagram(s) may represent methods in accordance with the disclosed subject matter when disparate entities enact disparate portions of the methods. Furthermore, not all illustrated acts may be required to implement a method in accordance with the subject specification. It should be further appreciated that the methods disclosed throughout the subject specification are capable of being stored on an article of manufacture to facilitate transporting and transferring such methods to computers for execution by a processor or for storage in a memory.

FIG. 6 illustrates a flow chart of an example method 600 for identifying and rendering content relevant to a user's current mental state and context in accordance with various aspects and embodiments described herein. At 602, user state attributes associated with a user's current state of mind during a current session of the user with a streaming media provider are determined based on at least one of: navigation of the streaming media provider by the user during the current session, media items provided by the streaming media provider that are played during the current session, or a manner via which the user interacts with or reacts to the played media items, wherein the state of the user includes a mood of the user (e.g., via state component 108).

For example, when a user is employing a search mechanism to find and watch videos related to repair a broken cell phone and the user repeatedly watches the beginning on the found videos before starting a new one, state component 108 can determine that the user is probably frustrated, annoyed, focused on finding a solution to a specific problem as opposed to looking for entertainment content and attentive to the current session. At 604, a media item provided by the streaming media provider is selected based on the user state attributes (e.g., via selection component 112). For example, selection component 112 can select a video trailer for a channel provided on by the streaming media provider that includes several short do it yourself repairs for different cell phone types and issues. In another example, selection component 112 can select a media advertisement for a service that repairs broken cell phones. At 604, the selected media item is then rendered to the user during the current session.

FIG. 7 illustrates a flow chart of another example method 700 for identifying and rendering content relevant to a user's current mental state and context in accordance with various aspects and embodiments described herein. At 702, mood attributes associated with a user's current mood during a session of the user with a streaming media provider and context attributes associated with a current context of the session based are determined on at least one of: navigation of the streaming media provider by the user during the current session, media items provided by the streaming media provider that are played during the current session, or an environment of the user (e.g., via state component 108 and context component 110). At 704 selecting a media item provided by the streaming media provider based on the mood attributes and the context attributes (e.g., via selection component 112). At 706, the media item is rendered to the user during the current session (e.g., via rendering component 204).

FIG. 8 illustrates a flow chart of another example method 700 for identifying and rendering content relevant to a user's current mental state and context in accordance with various aspects and embodiments described herein. At 802, current mood attributes associated with a user's current mood during a session of the user with a streaming media provider and current context attributes associated with a current context of the session are determined based on at least one of: navigation of the streaming media provider by the user during the current session, media items provided by the streaming media provider that are played during the current session, or an environment of the user (e.g., via state component 108 and context component 110). At 804, a plurality of media advertisements provided by the streaming media provider are scored based on relevance and suitability for the user during the user's session, wherein the relevance and suitability is based on a correspondence between the current mood and current context attributes, and state and context attributes respectively associated with the plurality of media advertisements (e.g., via scoring component 202). At 806, one of the plurality of media advertisements associated with a score exceeding a threshold score is selected, wherein scores above the threshold score indicate a high degree of relevance and suitability for the user based on the user's current mood and the current context of the session (e.g., via selection component 112). At 808, streaming of the media advertisement to the user is effectuated during the user's current session (e.g., via rendering component 204).

Example Operating Environments

The systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which may be explicitly illustrated in this disclosure.

Figure 10:
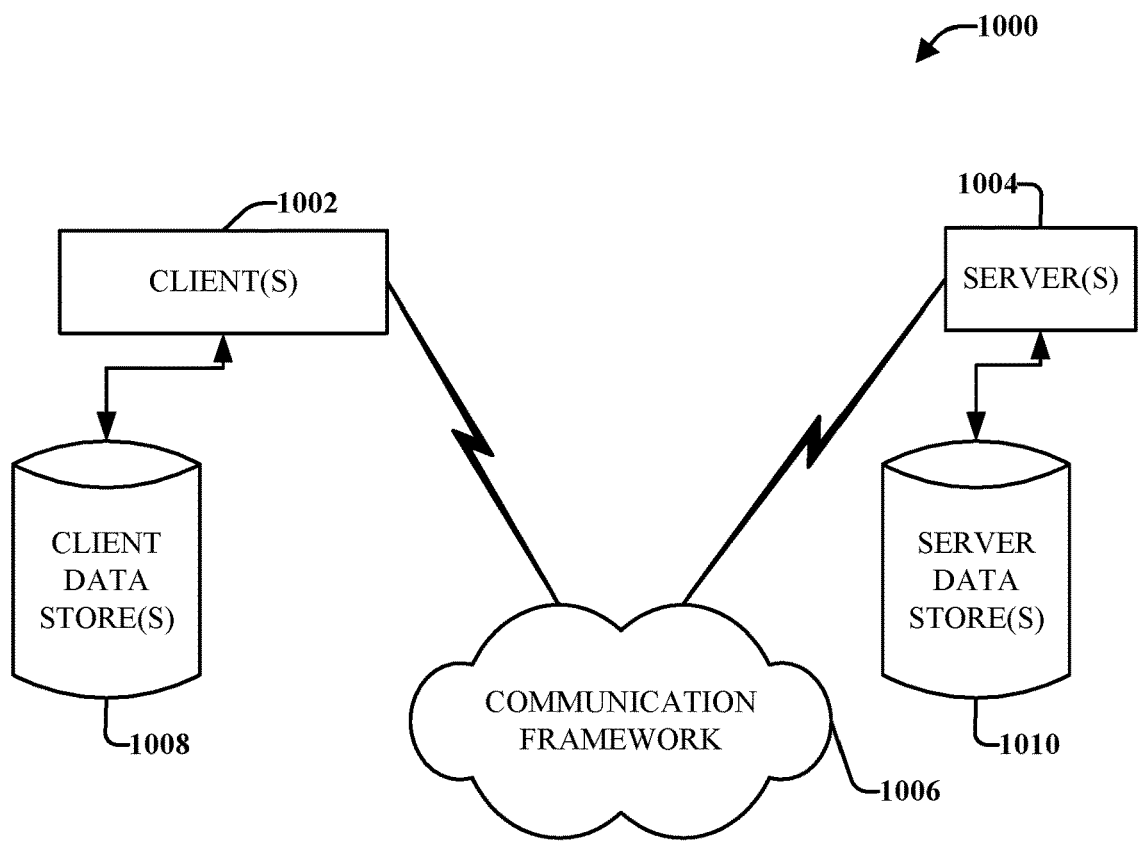
FIG. 10 is a schematic block diagram of a sample-computing environment in accordance with various aspects and embodiments.

With reference to FIG. 10, a suitable environment 1000 for implementing various aspects of the claimed subject matter includes a computer 1002. The computer 1002 includes a processing unit 1004, a system memory 1006, a codec 1005, and a system bus 1008. The system bus 1008 couples system components including, but not limited to, the system memory 1006 to the processing unit 1004. The processing unit 1004 can be any of various available processors. Dual microprocessors and other multiprocessor architectures also can be employed as the processing unit 1004.

The system bus 1008 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 13104), and Small Computer Systems Interface (SCSI).

The system memory 1006 includes volatile memory 1010 and non-volatile memory 1012. The basic input/output system (BIOS), containing the basic routines to transfer information between elements within the computer 1002, such as during start-up, is stored in non-volatile memory 1012. In addition, according to present innovations, codec 1005 may include at least one of an encoder or decoder, wherein the at least one of an encoder or decoder may consist of hardware, a combination of hardware and software, or software. Although, codec 1005 is depicted as a separate component, codec 1005 may be contained within non-volatile memory 1012. By way of illustration, and not limitation, non-volatile memory 1012 can include read only memory (ROM), programmable ROM (PROM), electrically programmable ROM (EPROM), electrically erasable programmable ROM (EEPROM), or flash memory. Volatile memory 1010 includes random access memory (RAM), which acts as external cache memory. According to present aspects, the volatile memory may store the write operation retry logic (not shown in FIG. 10) and the like. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM.

Computer 1002 may also include removable/non-removable, volatile/non-volatile computer storage medium. FIG. 10 illustrates, for example, disk storage 1014. Disk storage 1014 includes, but is not limited to, devices like a magnetic disk drive, solid state disk (SSD) floppy disk drive, tape drive, Jaz drive, Zip drive, LS-70 drive, flash memory card, or memory stick. In addition, disk storage 1014 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1014 to the system bus 1008, a removable or non-removable interface is typically used, such as interface 1016.

It is to be appreciated that FIG. 10 describes software that acts as an intermediary between users and the basic computer resources described in the suitable operating environment 1000. Such software includes an operating system 1018. Operating system 1018, which can be stored on disk storage 1014, acts to control and allocate resources of the computer system 1002. Applications 1020 take advantage of the management of resources by operating system 1018 through program modules 1024, and program data 1026, such as the boot/shutdown transaction table and the like, stored either in system memory 1006 or on disk storage 1014. It is to be appreciated that the claimed subject matter can be implemented with various operating systems or combinations of operating systems.

A user enters commands or information into the computer 1002 through input device(s) 1028. Input devices 1028 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1004 through the system bus 1008 via interface port(s) 1030. Interface port(s) 1030 include, for example, a serial port, a parallel port, a game port, and a universal serial bus (USB). Output device(s) 1036 use some of the same type of ports as input device(s). Thus, for example, a USB port may be used to provide input to computer 1002, and to output information from computer 1002 to an output device 1036. Output adapter 1034 is provided to illustrate that there are some output devices 1036 like monitors, speakers, and printers, among other output devices 1036, which require special adapters. The output adapters 1034 include, by way of illustration and not limitation, video and sound cards that provide a means of connection between the output device 1036 and the system bus 1008. It should be noted that other devices and/or systems of devices provide both input and output capabilities such as remote computer(s) 1038.

Computer 1002 can operate in a networked environment using logical connections to one or more remote computers, such as remote computer(s) 1038. The remote computer(s) 1038 can be a personal computer, a server, a router, a network PC, a workstation, a microprocessor based appliance, a peer device, a smart phone, a tablet, or other network node, and typically includes many of the elements described relative to computer 1002. For purposes of brevity, only a memory storage device 1040 is illustrated with remote computer(s) 1038. Remote computer(s) 1038 is logically connected to computer 1002 through a network interface 1042 and then connected via communication connection(s) 1044. Network interface 1042 encompasses wire and/or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1044 refers to the hardware/software employed to connect the network interface 1042 to the bus 1008. While communication connection 1044 is shown for illustrative clarity inside computer 1002, it can also be external to computer 1002. The hardware/software necessary for connection to the network interface 1042 includes, for exemplary purposes only, internal and external technologies such as, modems including regular telephone grade modems, cable modems and DSL modems, ISDN adapters, and wired and wireless Ethernet cards, hubs, and routers.

Referring now to FIG. 11, there is illustrated a schematic block diagram of a computing environment 1100 in accordance with this disclosure. The system 1100 includes one or more client(s) 1102 (e.g., laptops, smart phones, PDAs, media players, computers, portable electronic devices, tablets, and the like). The client(s) 1102 can be hardware and/or software (e.g., threads, processes, computing devices). The system 1100 also includes one or more server(s) 1104. The server(s) 1104 can also be hardware or hardware in combination with software (e.g., threads, processes, computing devices). The servers 1104 can house threads to perform transformations by employing aspects of this disclosure, for example. One possible communication between a client 1102 and a server 1104 can be in the form of a data packet transmitted between two or more computer processes wherein the data packet may include video data. The data packet can include a metadata, e.g., associated contextual information, for example. The system 1100 includes a communication framework 1106 (e.g., a global communication network such as the Internet, or mobile network(s)) that can be employed to facilitate communications between the client(s) 1102 and the server(s) 1104.

Communications can be facilitated via a wired (including optical fiber) and/or wireless technology. The client(s) 1102 include or are operatively connected to one or more client data store(s) 1108 that can be employed to store information local to the client(s) 1102 (e.g., associated contextual information). Similarly, the server(s) 1104 are operatively include or are operatively connected to one or more server data store(s) 1110 that can be employed to store information local to the servers 1104.

In one embodiment, a client 1102 can transfer an encoded file, in accordance with the disclosed subject matter, to server 1104. Server 1104 can store the file, decode the file, or transmit the file to another client 1102. It is to be appreciated, that a client 1102 can also transfer uncompressed file to a server 1104 and server 1104 can compress the file in accordance with the disclosed subject matter. Likewise, server 1104 can encode video information and transmit the information via communication framework 1106 to one or more clients 1102.

The illustrated aspects of the disclosure may also be practiced in distributed computing environments where certain tasks are performed by remote processing devices that are linked through a communications network. In a distributed computing environment, program modules can be located in both local and remote memory storage devices.

Moreover, it is to be appreciated that various components described in this description can include electrical circuit(s) that can include components and circuitry elements of suitable value in order to implement the embodiments of the subject innovation(s). Furthermore, it can be appreciated that many of the various components can be implemented on one or more integrated circuit (IC) chips. For example, in one embodiment, a set of components can be implemented in a single IC chip. In other embodiments, one or more of respective components are fabricated or implemented on separate IC chips.

What has been described above includes examples of the embodiments of the present invention. It is, of course, not possible to describe every conceivable combination of components or methodologies for purposes of describing the claimed subject matter, but it is to be appreciated that many further combinations and permutations of the subject innovation are possible. Accordingly, the claimed subject matter is intended to embrace all such alterations, modifications, and variations that fall within the spirit and scope of the appended claims. Moreover, the above description of illustrated embodiments of the subject disclosure, including what is described in the Abstract, is not intended to be exhaustive or to limit the disclosed embodiments to the precise forms disclosed. While specific embodiments and examples are described in this disclosure for illustrative purposes, various modifications are possible that are considered within the scope of such embodiments and examples, as those skilled in the relevant art can recognize.

In particular and in regard to the various functions performed by the above described components, devices, circuits, systems and the like, the terms used to describe such components are intended to correspond, unless otherwise indicated, to any component which performs the specified function of the described component (e.g., a functional equivalent), even though not structurally equivalent to the disclosed structure, which performs the function in the disclosure illustrated exemplary aspects of the claimed subject matter. In this regard, it will also be recognized that the innovation includes a system as well as a computer-readable storage medium having computer-executable instructions for performing the acts and/or events of the various methods of the claimed subject matter.

The aforementioned systems/circuits/modules have been described with respect to interaction between several components/blocks. It can be appreciated that such systems/circuits and components/blocks can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described in this disclosure may also interact with one or more other components not specifically described in this disclosure but known by those of skill in the art.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

As used in this application, the terms "component," "module," "system," or the like are generally intended to refer to a computer-related entity, either hardware (e.g., a circuit), a combination of hardware and software, software, or an entity related to an operational machine with one or more specific functionalities. For example, a component may be, but is not limited to being, a process running on a processor (e.g., digital signal processor), a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers. Further, a "device" can come in the form of specially designed hardware; generalized hardware made specialized by the execution of software thereon that enables the hardware to perform specific function; software stored on a computer readable storage medium; software transmitted on a computer readable transmission medium; or a combination thereof.

Moreover, the words "example" or "exemplary" are used in this disclosure to mean serving as an example, instance, or illustration. Any aspect or design described in this disclosure as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Computing devices typically include a variety of media, which can include computer-readable storage media and/or communications media, in which these two terms are used in this description differently from one another as follows. Computer-readable storage media can be any available storage media that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

On the other hand, communications media typically embody computer-readable instructions, data structures, program modules or other structured or unstructured data in a data signal that can be transitory such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

In view of the exemplary systems described above, methodologies that may be implemented in accordance with the described subject matter will be better appreciated with reference to the flowcharts of the various figures. For simplicity of explanation, the methodologies are depicted and described as a series of acts. However, acts in accordance with this disclosure can occur in various orders and/or concurrently, and with other acts not presented and described in this disclosure. Furthermore, not all illustrated acts may be required to implement the methodologies in accordance with certain aspects of this disclosure. In addition, those skilled in the art will understand and appreciate that the methodologies could alternatively be represented as a series of interrelated states via a state diagram or events. Additionally, it should be appreciated that the methodologies disclosed in this disclosure are capable of being stored on an article of manufacture to facilitate transporting and transferring such methodologies to computing devices. The term article of manufacture, as used in this disclosure, is intended to encompass a computer program accessible from any computer-readable device or storage media.

What is claimed is:

1. A method, comprising:
   collecting information specifying a length of media items presented to a user, by a streaming media player, during a current viewing session of the user;
   determining streaming media currently being viewed by other users, that are socially connected to the user, during the user's current viewing session;
   selecting a subsequent media item to provide to the user, through the streaming media player, based on the length of media items presented to the user and the streaming media currently being viewed by the other users during the user's current viewing session; and
   effectuating streaming of the subsequent media item to the user through the streaming media player.

2. The method of claim 1, comprising collecting information specifying a length of media items being viewed by the other users during separate viewing sessions concurrent with the current viewing session.

3. The method of claim 2, comprising:
   determining a current state of mind of each particular user among the other users based on a length of media items being presented by a streaming media player in each of the separate viewing sessions, including determining that the particular user is in an entertainment state when the length of the media items is longer in duration and determining that the particular user is in a work related state when the length of the media items is shorter in duration; and
   selecting a subsequent media item to provide through the streaming media player to the user based on the current states of mind of the one or more other users.

4. The method of claim 2, wherein each of the other users socially connected to the user is a friend of the user, shares similar preferences to the user, or shares demographics with the user.

5. The method of claim 2, comprising determining a current state of mind of the user based on the length of media items being presented to the user by a streaming media player, including determining that the user is in an entertainment state when the length of the media items is longer in duration and determining that the user is in a work related state when the length of the media items is shorter in duration.

6. The method of claim 5, comprising selecting a subsequent media item to provide through the streaming media player based on the determined current state of mind of the user and information specifying a length of media items presented to the other users during separate viewing sessions concurrent with the current viewing session.

7. The method of claim 1, wherein effectuating streaming of the subsequent media item to the user through the streaming media player comprises effectuating presentation of the subsequent media item in one of a recommendation section or a list of media items recommended to the user during the user's current viewing session.

8. A system, comprising:
   a data store storing data collected by a communications server;
   the communications server, wherein the communications server is in communication with a client device and a content provider, and performs operations including:
     collecting information specifying a length of media items presented to a user, by a streaming media player, during a current viewing session of the user;
     determining streaming media currently being viewed by other users, that are socially connected to the user, during the user's current viewing session;
     selecting a subsequent media item to provide to the user, through the streaming media player, based on the length of media items presented to the user and the streaming media being viewed by the other users during the user's current viewing session; and
     effectuating streaming of the subsequent media item to the user through the streaming media player.

9. The system of claim 8, the operations comprising collecting information specifying a length of media items being viewed by the other users during separate viewing sessions concurrent with the current viewing session.

10. The system of claim 9, the operations comprising:
    determining a current state of mind of each particular user among the other users based on a length of media items being presented by a streaming media player in each of the separate viewing sessions, including determining that the particular user is in an entertainment state when the length of the media items is longer in duration and determining that the particular user is in a work related state when the length of the media items is shorter in duration; and
    selecting a subsequent media item to provide through the streaming media player to the user based on the current states of mind of the one or more other users.

11. The system of claim 9, wherein each of the other users socially connected to the user is a friend of the user, shares similar preferences to the user, or shares demographics with the user.

12. The system of claim 9, the operations comprising determining a current state of mind of the user based on the length of media items being presented to the user by a streaming media player, including determining that the user is in an entertainment state when the length of the media items is longer in duration and determining that the user is in a work related state when the length of the media items is shorter in duration.

13. The system of claim 12, the operations comprising selecting a subsequent media item to provide through the streaming media player based on the determined current state of mind of the user and information specifying a length of media items presented to the other users during separate viewing sessions concurrent with the current viewing session.

14. The system of claim 8, wherein effectuating streaming of the subsequent media item to the user through the streaming media player comprises effectuating presentation of the subsequent media item in one of a recommendation section or a list of media items recommended to the user during the user's current viewing session.

15. A non-transitory computer readable medium storing instructions that when executed by one or more computing devices, cause the one or more computing devices to perform operations comprising:
- collecting information specifying a length of media items presented to a user, by a streaming media player, during a current viewing session of the user;
- determining streaming media currently being viewed by other users, that are socially connected to the user, during the user's current viewing session;
- selecting a subsequent media item to provide to the user, through the streaming media player, based on the length of media items presented to the user and the streaming media currently being viewed by the other users during the user's current viewing session; and
- effectuating streaming of the subsequent media item to the user through the streaming media player.

16. The non-transitory computer readable medium of claim 15, comprising collecting information specifying a length of media items being viewed by the other users during separate viewing sessions concurrent with the current viewing session.

17. The non-transitory computer readable medium of claim 16, comprising:
- determining a current state of mind of each particular user among the other users based on a length of media items being presented by a streaming media player in each of the separate viewing sessions, including determining that the particular user is in an entertainment state when the length of the media items is longer in duration and determining that the particular user is in a work related state when the length of the media items is shorter in duration; and
- selecting a subsequent media item to provide through the streaming media player to the user based on the current states of mind of the one or more other users.

18. The non-transitory computer readable medium of claim 16, wherein each of the other users socially connected to the user is a friend of the user, shares similar preferences to the user, or shares demographics with the user.

19. The non-transitory computer readable medium of claim 16, comprising determining a current state of mind of the user based on the length of media items being presented to the user by a streaming media player, including determining that the user is in an entertainment state when the length of the media items is longer in duration and determining that the user is in a work related state when the length of the media items is shorter in duration.

20. The non-transitory computer readable medium of claim 19, comprising selecting a subsequent media item to provide through the streaming media player based on the determined current state of mind of the user and information specifying a length of media items presented to the other users during separate viewing sessions concurrent with the current viewing session.

* * * * *